United States Patent
Delso

(10) Patent No.: US 10,677,873 B2
(45) Date of Patent: Jun. 9, 2020

(54) SYSTEM AND METHOD FOR CORRECTING AN ARTIFACT WITHIN MAGNETIC RESONANCE DATA

(71) Applicant: GENERAL ELECTRIC COMPANY, Schenectady, NY (US)

(72) Inventor: Gaspar Delso, Cambridge (GB)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 325 days.

(21) Appl. No.: 15/689,157

(22) Filed: Aug. 29, 2017

(65) Prior Publication Data

US 2019/0064298 A1 Feb. 28, 2019

(51) Int. Cl.

| | |
|---|---|
| G01R 33/565 | (2006.01) |
| A61B 5/055 | (2006.01) |
| A61B 5/00 | (2006.01) |
| G01R 33/48 | (2006.01) |
| G01R 33/56 | (2006.01) |
| A61B 6/03 | (2006.01) |

(52) U.S. Cl.
CPC .......... *G01R 33/565* (2013.01); *A61B 5/0035* (2013.01); *A61B 5/055* (2013.01); *A61B 5/7203* (2013.01); *A61B 6/037* (2013.01); *A61B 2576/00* (2013.01); *G01R 33/481* (2013.01); *G01R 33/5608* (2013.01)

(58) Field of Classification Search
CPC ... A61B 2576/00; A61B 5/0035; A61B 5/055; A61B 5/7203; A61B 6/037; G01R 33/481; G01R 33/5608; G01R 33/565; G01R 33/56; G01R 33/56536; G06T 7/0012

See application file for complete search history.

(56) References Cited

U.S. PATENT DOCUMENTS

| | | |
|---|---|---|
| 2013/0182008 A1 | 7/2013 | Zhou et al. |
| 2014/0072196 A1 | 3/2014 | Hwang et al. |
| 2015/0332461 A1 | 11/2015 | Kim et al. |
| 2016/0018502 A1 | 1/2016 | Wang et al. |

(Continued)

FOREIGN PATENT DOCUMENTS

KR 10-2013-0130555 A 12/2013

OTHER PUBLICATIONS

International Search Report and Written Opinion issued in connection with corresponding PCT Application No. PCT/US2018/043275 dated Nov. 7, 2018, 11 pages.

(Continued)

*Primary Examiner* — Rishi R Patel
(74) *Attorney, Agent, or Firm* — Grogan, Tuccillo & Vanderleeden, LLP

(57) ABSTRACT

A system for correcting an artifact within MR data is provided. The system includes a magnet assembly and a controller in electronic communication with the magnet assembly. The controller is operative to: acquire the MR data from a subject via the magnet assembly, the MR data having a first portion and a second portion, the first portion including the artifact; and to populate the first portion of the MR data with substitute data corresponding to the second portion. The first portion corresponds to a first region of the subject, and the second portion corresponds to a second region of the subject that is anatomically symmetrical to the first region.

20 Claims, 8 Drawing Sheets

(56) References Cited

U.S. PATENT DOCUMENTS

| | | | |
|---|---|---|---|
| 2016/0025832 A1* | 1/2016 | Piron | G01R 33/565 |
| | | | 324/322 |
| 2016/0148351 A1* | 5/2016 | Hilbert | G01R 33/5608 |
| | | | 382/131 |
| 2018/0256042 A1* | 9/2018 | Beckers | G16H 30/40 |

OTHER PUBLICATIONS

Schramm, et al.;Evaluation and automatic correction of metal-implant-induced artifacts in MR-based attenuation correction in whole-body PET/MR imaging; Institute of Physics and Engineering in Medicine; p. 2713-2726; 2014.

Burger, et al.; Hybrid PET/MR Imaging: An Algorithm to Reduce Metal Artifacts from Dental Implants in Dixon-Based Attenuation Map Generation Using a Multiacquisition Variable-Resonance Image Combination Sequence; GE Healthcare Ltd., Jul. 5, 2017.

Fuin, et al.; PET/MR in the Presence of Metal Implants: Completion of the Attenuation Map from PET Emission Data; GE Healthcare Ltd., Jul. 5, 2017.

Ladefoged, et al.; Automatic correction of dental artifacts in PET/MRI; Journal of Medical Imaging; Apr.-Jun. 2015.

Gunzinger, et al.; Metal artifact reduction in patients with dental implants using multispectral three-dimensional data acquisition for hybrid PET/MRI; EJNMMI Physics; 2014.

* cited by examiner

SYSTEM AND METHOD FOR CORRECTING AN ARTIFACT WITHIN MAGNETIC RESONANCE DATA

BACKGROUND

Technical Field

Embodiments of the invention relate generally to medical imaging systems, and more specifically, to a system and method for correcting an artifact within magnetic resonance ("MR") data.

Discussion of Art

Positron Emission Tomography ("PET") imaging involves the creation of tomographic images of positron emitting radionuclides in a subject of interest. A radionuclide-labeled agent is administered to a subject positioned within a detector ring. As the radionuclides decay, positively charged electrons known as "positrons" are emitted therefrom. As these positrons travel through the tissues of the subject, they lose kinetic energy and ultimately collide with an electron, resulting in mutual annihilation. The positron annihilation results in a pair of oppositely-directed gamma rays being emitted at approximately 511 keV, which are subsequently detected by scintillators in the detector ring. When struck by a gamma ray, each scintillator illuminates, activating a photovoltaic component, such as a photodiode.

The signals from the photovoltaics are processed as incidences of gamma rays. When two gamma rays strike oppositely positioned scintillators at approximately the same time, a coincidence is registered. Data sorting units process the coincidences to determine true coincidence events and to sort out data representing dead times and single gamma ray detections. The coincidence events are binned and integrated to form frames of PET data which may be reconstructed into images depicting the distribution of the radionuclide-labeled agent and/or metabolites thereof in the subject. As will be appreciated, however, it is often necessary to estimate and correct for the attenuation of the gamma rays due to the imaged subject itself.

One approach to estimate such attenuation involves magnetic resonance imaging ("MRI") the subject, in conjunction with a PET scan, to obtain a model of the structure of the imaged subject. MRI obtains digitized visual images representing the internal structure of subjects having substantial populations of atomic nuclei that are susceptible to nuclear magnetic resonance ("NMR"). Many MRI systems use magnet assemblies that house superconductive magnets to impose a strong main magnetic field on the nuclei in the patient/object to be imaged within a target volume (hereinafter also referred to as the "imaging bore" and/or simply "bore"). The nuclei are excited by a radio frequency ("RF") signal typically transmitted via an RF coil at characteristics NMR (Larmor) frequencies. By spatially disturbing localized magnetic fields surrounding the subject within the imaging bore, the nuclei emit RF responses (also referred to herein as the "MR signal") as the excited protons relax back to their lower energy normal state. The MR signal is sensed and typically stored as MR data within k-space such that a map or image of the nuclei responses as a function of their spatial location may be generated and displayed. As will be appreciated, an image of the nuclei responses provides a non-invasive view of an subjects' internal structure, which in turn can be used to estimate the attenuation of gamma rays from a PET scan.

Many MRI systems, however, will experience artifacts, i.e., corruption and/or degradation of the MR signal, when imaging a subject that contains metal, e.g., a patient with a dental implant. Such artifacts usually appear as gaping holes on an MRI image, which, if left uncorrected, may degrade the ability to estimate the structure of the subject for the purpose of correcting gamma ray attenuation.

What is needed, therefore, is an improved system and method for correcting an artifact within MR data.

BRIEF DESCRIPTION

In an embodiment, a system for correcting an artifact within MR data is provided. The system includes a magnet assembly and a controller in electronic communication with the magnet assembly. The controller is operative to: acquire the MR data from a subject via the magnet assembly, the MR data having a first portion and a second portion, the first portion including the artifact; and to populate the first portion of the MR data with substitute data corresponding to the second portion. The first portion corresponds to a first region of the subject, and the second portion corresponds to a second region of the subject that is anatomically symmetrical to the first region.

In another embodiment, a method for correcting an artifact within MR data is provided. The method includes: acquiring the MR data from a subject via a magnet assembly in electronic communication with a controller, the MR data having a first portion and a second portion, the first portion including the artifact; and populating, via the controller, the first portion of the MR data with substitute data corresponding to the second portion. The first portion corresponds to a first region of the subject, and the second portion corresponds to a second region of the subject that is anatomically symmetrical to the first region.

In yet another embodiment, a non-transitory computer readable medium storing instructions is provided. The stored instructions are configured to adapt a controller to: acquire MR data from a subject via a magnet assembly, the MR data having a first portion and a second portion, the first portion including an artifact; and to populate the first portion of the MR data with substitute data corresponding to the second portion. The first portion corresponds to a first region of the subject, and the second portion corresponds to a second region of the subject that is anatomically symmetrical to the first region.

DRAWINGS

The present invention will be better understood from reading the following description of non-limiting embodiments, with reference to the attached drawings, wherein below:

DETAILED DESCRIPTION

Figure 1:
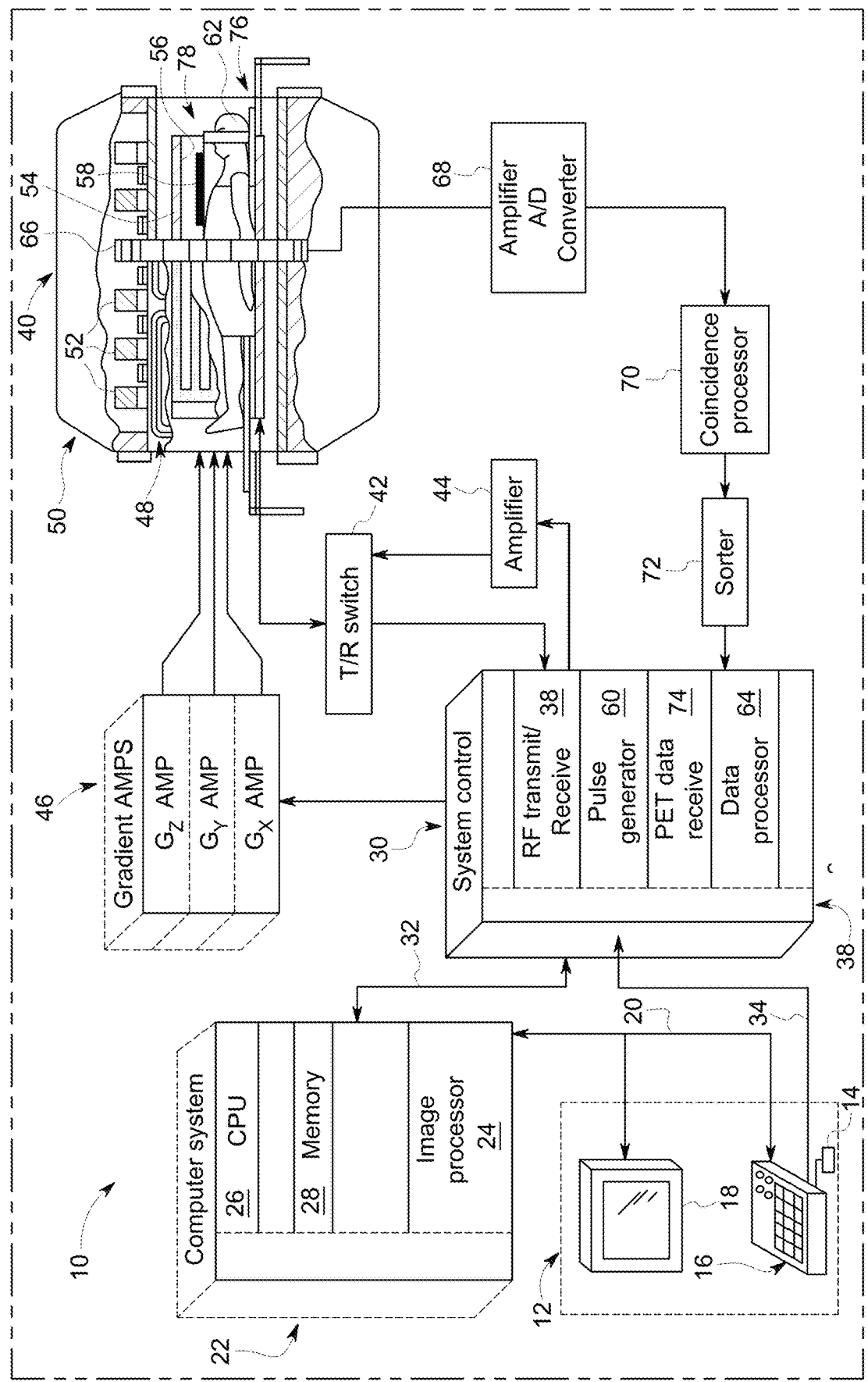
FIG. 1 is a schematic diagram of a system for correcting an artifact within MR data, in accordance with an embodiment of the invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process. The term "MR data," as used herein, refers to data, e.g., raw k-space and/or image space, derived from an MR signal. As further used herein, the term "attenuation correction" means a process and/or algorithm that corrects/accounts for the distortion in PET imaging resulting from the loss of detection events due to absorption and/or scattering of gamma rays produced from the decay of a radionuclide-labeled agent that has been injected into a subject/object to be imaged. The term "anatomically symmetrical," as used herein, means having mirrored, or substantially mirrored, structures, e.g., the left side of a normal human face is typically anatomically symmetrical to the right side of the same human face.

Additionally, while the embodiments disclosed herein are described with respect to an PET-MRI based imaging system, it is to be understood that embodiments of the present invention are equally applicable to other devices and/or imaging systems which rely on MRI and/or which experience artifacts and/or similar distortions. Further, embodiments of the present invention related imaging systems may be used to analyze objects within any material which can be internally imaged, generally. As such, embodiments of the present invention are not limited to analyzing objects within human tissue.

Referring now to FIG. 1, the major components of a hybrid PET-MRI system 10 that incorporates embodiments of the present invention are shown. As will be appreciated and described below, the PET-MRI system 10 combines both a PET sub-system and an MRI sub-system. The operation of the system 10 may be controlled from an operator console 12 which includes a keyboard or other input device 14, a control panel 16, and a display screen 18. The console 12 communicates through a link 20 with a separate computer system 22 that enables an operator to control the production and display of images on the display screen 18. The computer system 22 includes a number of modules, such as an image processor module 24, a CPU module 26, and a memory module 28. The computer system 22 may also be connected to permanent or back-up memory storage, a network, or may communicate with a separate system controller 30 through link 32. The input device 14 can include a mouse, keyboard, track ball, touch activated screen, light wand, or any similar or equivalent input device, and may be used for interactive geometry prescription.

The system controller 30 includes a set of modules in communication with one another and connected to the operator console 12 through link 34. It is through link 32 that the system controller 30 receives commands to indicate the scan sequence or sequences that are to be performed. For MRI data acquisition, an RF transmit/receive module 38 commands the scanner 40 to carry out the desired scan sequence, by sending instructions, commands, and/or requests describing the timing, strength and shape of the RF pulses and pulse sequences to be produced, to correspond to the timing and length of the data acquisition window. In this regard, a transmit/receive switch 42 controls the flow of data via amplifier 44 to scanner 40 from RF transmit module 38, and from scanner 40 to RF receive module 38. The system controller 30 also connects to a gradient amplifier sub-system 46, having amplifiers $G_x$, $G_y$, and $G_z$, to indicate the timing and shape of the gradient pulses that are produced during the scan.

The gradient waveform instructions produced by system controller 30 are sent to the gradient amplifier sub-system 46 which may be external of the scanner 40 or of the system controller 30, or may be integrated therein. Each gradient amplifier, $G_x$, $G_y$, and $G_z$, excites a corresponding physical gradient coil in a gradient coil assembly generally designated 48 to produce the magnetic field gradients used for spatially encoding acquired signals. The gradient coil assembly 48 forms part of a magnet assembly 50 which includes a polarizing magnet 52 and an RF coil assembly 54. Alternatively, the gradient coils of gradient coil assembly 48 may be independent of the magnet assembly 50. In embodiments, the RF coil assembly 54 may include a whole-body RF transmit coil 56. As will be appreciated, coil 56 of the RF coil assembly 54 may be configured for transmitting RF pulses while a separate surface coil 58 is configured to receive RF signals. A pulse generator 60 may be integrated into the system controller 30 as shown, or may be integrated into the MRI scanner 40, to produce pulse sequences or pulse sequence signals for the gradient amplifiers 46 and/or the RF coil assembly 54. In addition, pulse generator 60 may generate PET data blanking signals synchronously with the production of the pulse sequences. These blanking signals may be generated on separate logic lines for subsequent data processing. The MR signals resulting from the excitation pulses, emitted by the excited nuclei in a patient/subject/imaged object 62, may be sensed by surface coil 58 and then transmitted to the RF transmit/receive module 38 via T/R switch 42. The MR signals are demodulated, filtered, and digitized in a data processing controller/processer 64 of the system controller 30.

Figure 4:
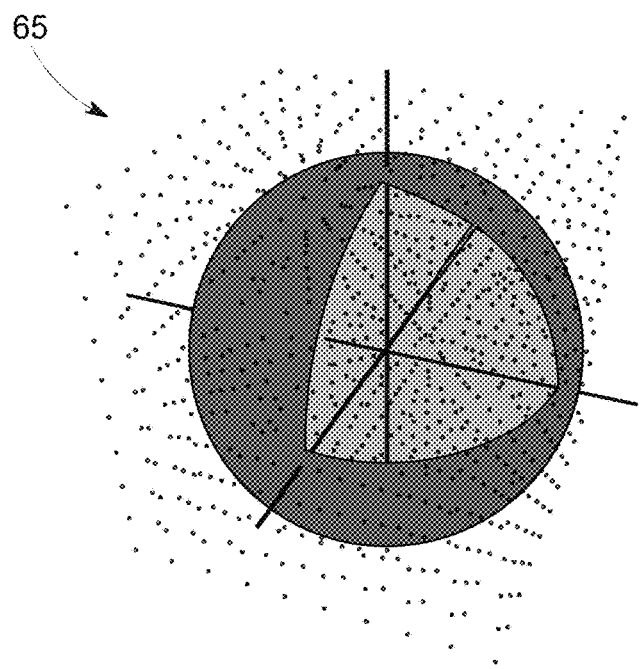
FIG. 4 is a diagram of MR data in a three-dimensional ("3D") space, acquired via the system of FIG. 1, in accordance with an embodiment of the invention.
Figure 5:
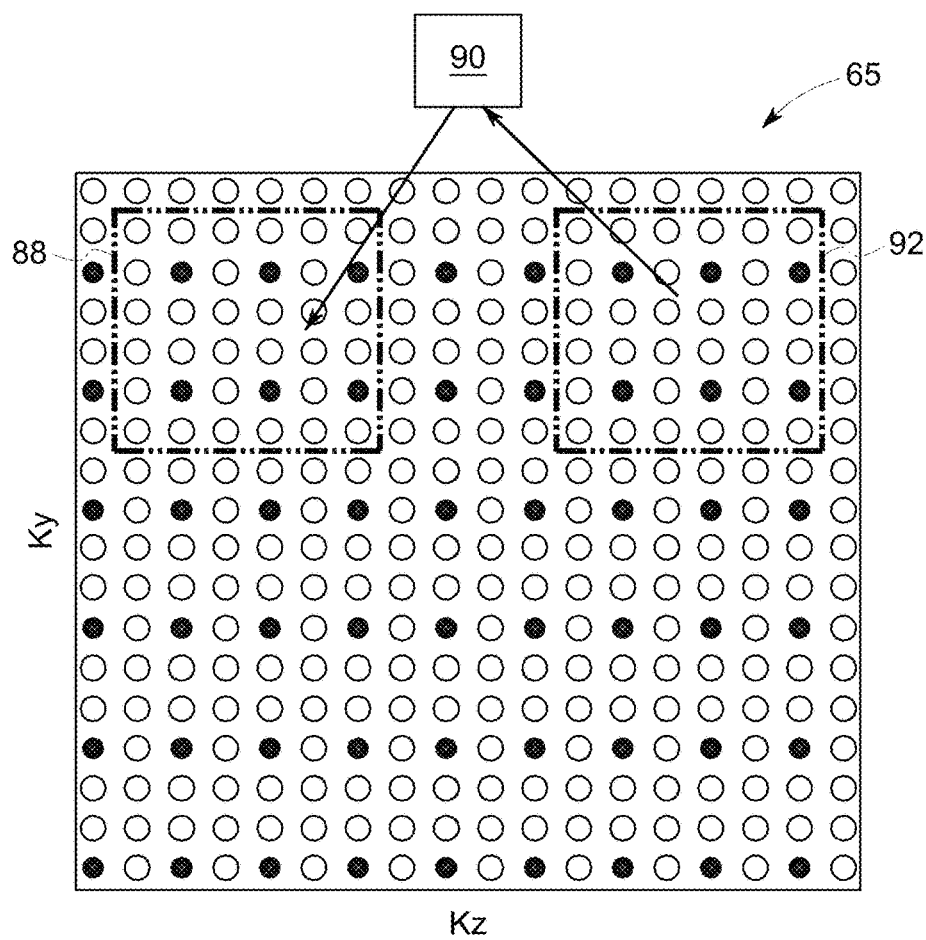
FIG. 5 is a diagram of a MR data in a two-dimensional ("2D") space, acquired via the system of FIG. 1, in accordance with an embodiment of the invention.

An MRI scan is complete when one or more sets of raw k-space/MR data 65 (FIGS. 4 and 5) has been acquired in the data processing controller 64. This raw k-space 65 data is reconstructed in data processing controller 64 which operates to transform the data (through Fourier or other techniques) into image data/space. This image data is conveyed through link 32 to the computer system 22 where it is stored in the memory module 28. Alternatively, in some embodiments, computer system 22 may assume the image data reconstruction and other functions of data processing controller 64. In response to commands received from the operator console 12, the image data stored in memory module 28 may be archived in long term storage or may be further processed by the image processor 24 or CPU 26, conveyed to the operator console 12, and presented on the display 18.

In combined PET-MRI systems, PET data may be acquired simultaneously with the MRI data acquisition described above. Thus, the scanner 40 also includes a positron emission detector array or ring 66 configured to detect gamma rays from positron annihilations emitted from the imaged subject 62. The detector ring 66 preferably includes a plurality of scintillators and photovoltaics arranged about a gantry. As will be appreciated, however, in embodiments, the detector array 66 may be of any suitable construction for acquiring PET data. In addition, the scintillator, photovoltaics, and other electronics of the detector ring 66 need not be shielded from the magnetic fields and/or RF fields applied by the polarizing magnet 52 and wholebody RF transmit coil 56. However, it is contemplated that embodiments of the present invention may include such shielding as known in the art, or may be combined with various other shielding techniques.

Gamma ray incidences detected by the detector ring 66 are transformed, by the photovoltaics of the detector ring 66, into electrical signals which are conditioned by a series of front end electronics 68. These conditioning circuits 68 may include various amplifiers, filters, and analog-to-digital converters. The digital signals outputted from the front end electronics 68 are then processed by a coincidence processor 70 to match gamma ray detections as potential coincidence events. When two gamma rays strike detectors approximately opposite one another, it is possible, absent the interactions of random noise and signal gamma ray detections, that a positron annihilation took place somewhere along the line between the detectors. Thus, the coincidences determined by coincidence processor 70 are sorted into true coincidence events and ultimately integrated by data sorter 72. The coincidence event data, or PET data, from sorter 72 is received by the system controller 30 at a PET data receive port 74 and stored in memory 28 for subsequent processing by the data processing controller 64. PET images may then be reconstructed by image processor 24 and combined with MR images to produce hybrid structural and metabolic or functional images. Conditioning circuits 68, coincidence processor 70, and sorter 72 may each be external of the scanner 40 or the system controller 30, or may be integrated therein.

Also included in PET-MR imaging system 10 is a patient support assembly/cradle 76 configured to support the patient/subject 62 within a bore 78 of the magnet assembly 50 during data acquisition. The patient cradle 76 enables movement of the patient 62 into various positions with respect to the magnet assembly 50, including a loading position outside the bore 78, and at least one imaging position, where at least a portion of the patient/subject 62 is positioned within an imaging volume (i.e., within the bore 78) when at the imaging position.

Figure 2:
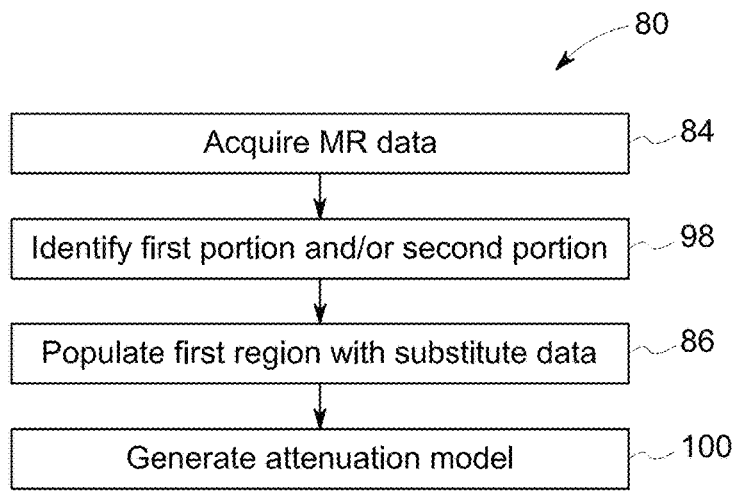
FIG. 2 is a flow chart depicting a method for correcting an artifact within MR data utilizing the system of FIG. 1, wherein the method includes identifying a first portion and/or a second portion of the MR data, in accordance with an embodiment of the invention.

Turning now to FIG. 2, a method 80 for correcting an artifact 82 (FIGS. 6 and 9) within MR data/k-Space 65 utilizing the system 10, in accordance with an embodiment of the invention, is shown. The method 80 includes acquiring 84 MR data 65 from a subject/object/patient 62, and populating 86 a first portion 88 (FIGS. 5, 6, and 9) of the MR data 65 with substitute data 90 (FIG. 5) that corresponds to a second portion 92 (FIGS. 5, 6, and 11) of the MR data 65. The first portion 88 corresponds to a first region 94 (FIGS. 6 and 9) of the subject 62, and the second portion 92 corresponds to a second region 96 (FIGS. 6 and 11) that is anatomically symmetrical to the first region 94. As further shown in FIG. 2, in embodiments, the method 80 may further include identifying 98 the first portion 88 and/or the second portion 92, and generating 100 an attenuation model based at least in part on the first portion 88 when populated with the substitute data 90.

As will be understood, acquiring 84 the MR data 65 may be performed/accomplished via the magnet assemble 50. In embodiments, the MR data 65 may be a 3D acquisition and/or a 2D acquisition.

Figure 3:
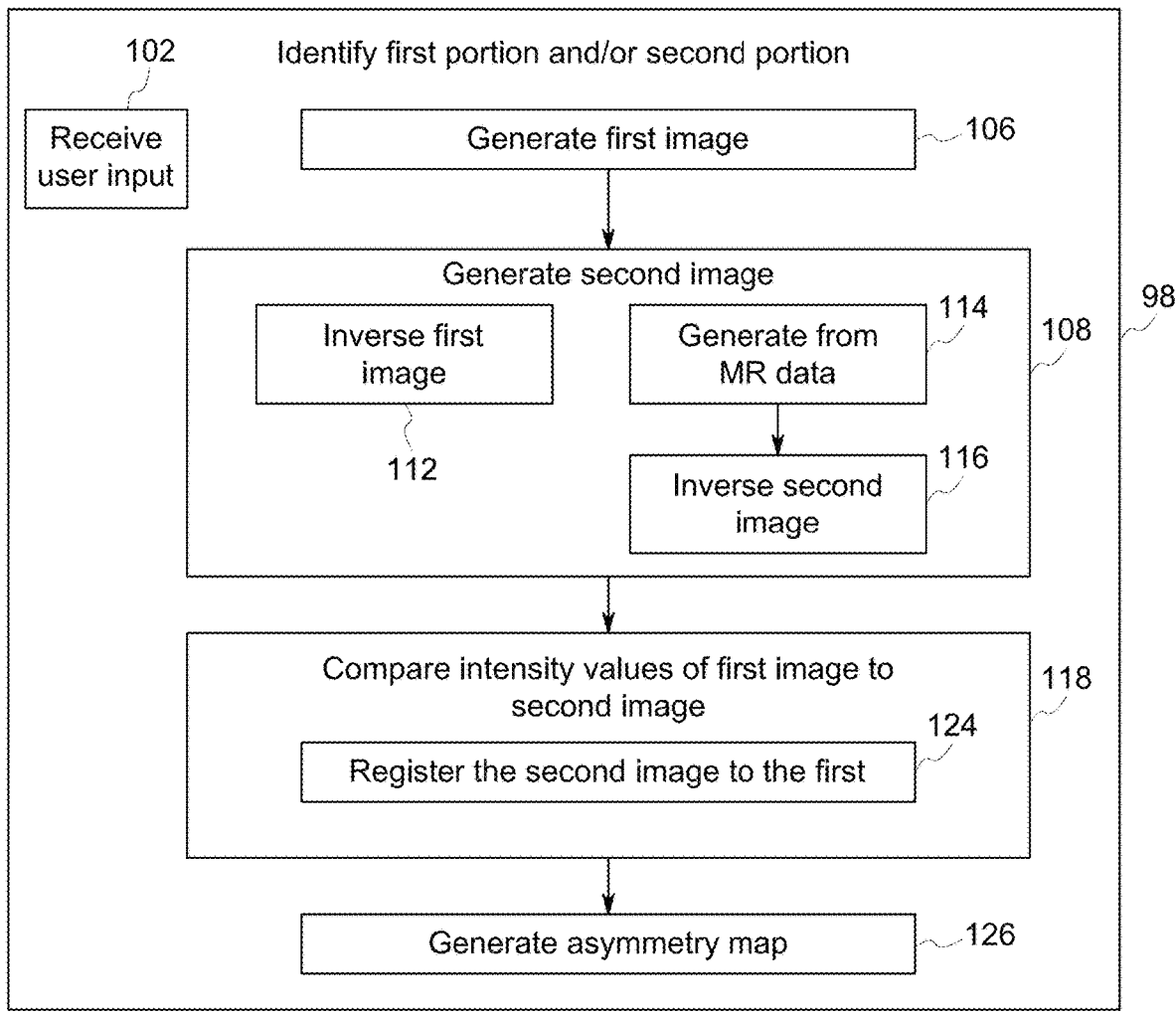
FIG. 3 is a flow chart depicting a sub-method for identifying the first portion and/or the second portion of MR data, in accordance with an embodiment of the invention.

Moving to FIG. 3, identifying 98 the first 88 and/or second 92 portions may be accomplished directly in k-space, and/or in transformed image space. In other words, the artifact 82 may be identified/located by locating large interconnected regions within k-space and/or image space, i.e., MR data 65, that have null, low, and/or otherwise distorted values.

In such embodiments, identifying 98 the first portion 88 may include receiving 102, via a user input device 14, an indicator that identifies the first 88 and/or second 92 portions, i.e., the system 10 may provide for manual and/or guided identification of the first portion 88. For example, a 2D and/or 3D depiction of k-space 65 may be displayed on a screen 18 such that a user/operator can use a mouse and/or touch screen to select the data points within k-space 65 which are to be included within the first 88 and/or second 92 portions. In other embodiments, identification 98 of the first portion 88 may be accomplished in image space by selecting a region 94 (FIG. 6) shown in an image 104 (FIG. 6), generated from k-space 65, which is affected by an artifact 82.

As further shown in FIG. 3, in embodiments, identification 98 of the first portion 88 may be accomplished/performed by the controller 30, i.e., the system 10 may provide for automatic identification of the first portion 88. In such embodiments, the controller 30 may identify 98 the first portion 88 by generating 106, 108 a first image 104 (FIGS. 6 and 9) and a second image 110 (FIGS. 7, 10, and 11). While the first image 104 may be generated 106 directly from the MR data 65, as will be appreciated, in embodiments, the second image 110 may be generated 108 based at least in part on/from the first image 104.

Figure 6:
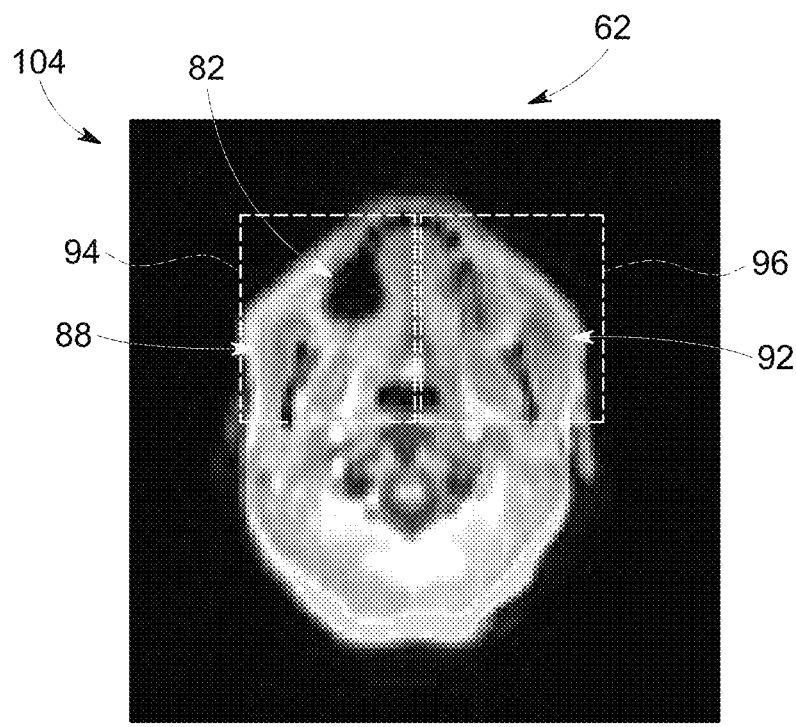
FIG. 6 is a diagram of a first image of a subject acquired via the system of FIG. 1, wherein the anatomy of the subject is symmetrical within the first image, in accordance with an embodiment of the invention.
Figure 7:
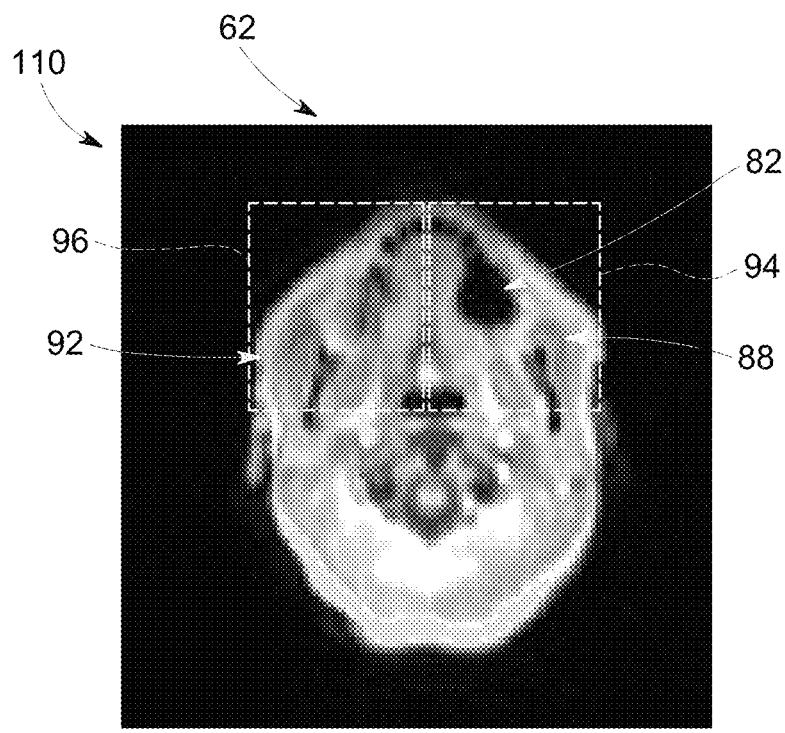
FIG. 7 is diagram of a second image of the subject of FIG. 6, wherein the second image is the inverse of the first image, in accordance with an embodiment of the invention.

Accordingly, as shown in FIGS. 6 and 7, in embodiments wherein the first image 104 depicts a symmetrical anatomy of the subject 62, such that the first image 104 includes both the first region 94 and the second region 96, the second image 110 may be generated 108 by inversing/flipping 112 (FIG. 3) the first image 104. For example, FIG. 6 shows the first image 104 depicting a top-down image of a patient's 62 jaw line such that the anatomy of the right side of the jaw, i.e., the second region 96, is substantially similar to the anatomy of the left side of the jaw, i.e., the first region 94. FIG. 7, in turn, depicts the second image 110 as an inverse of the first image 104.

Figure 9:
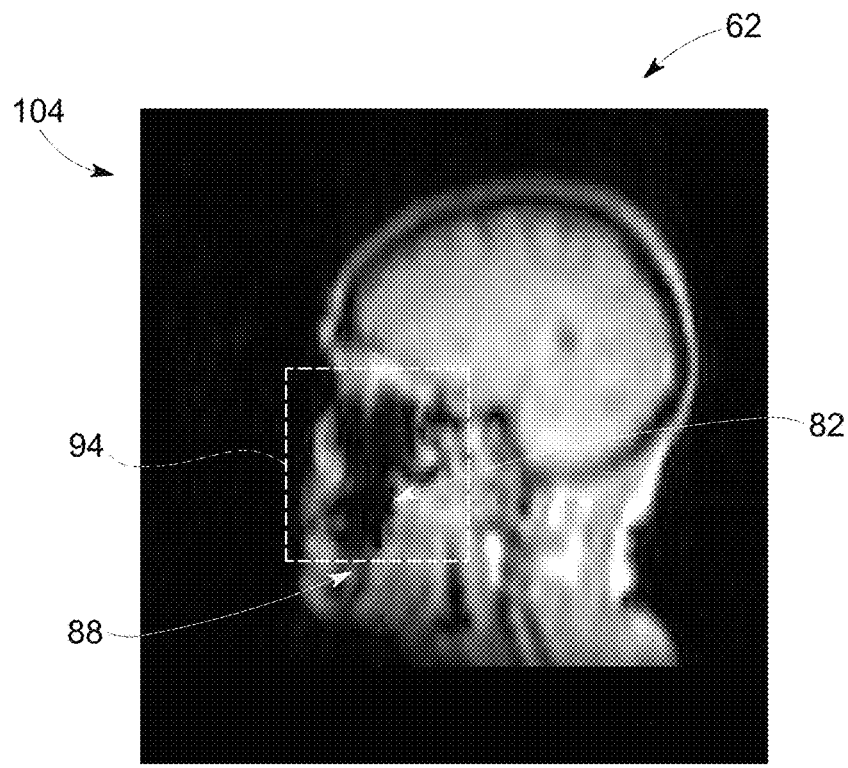
FIG. 9 is another diagram of the first image of a subject acquired via the system of FIG. 1, wherein the anatomy of the subject is asymmetrical within the first image, in accordance with an embodiment of the invention.
Figure 10:
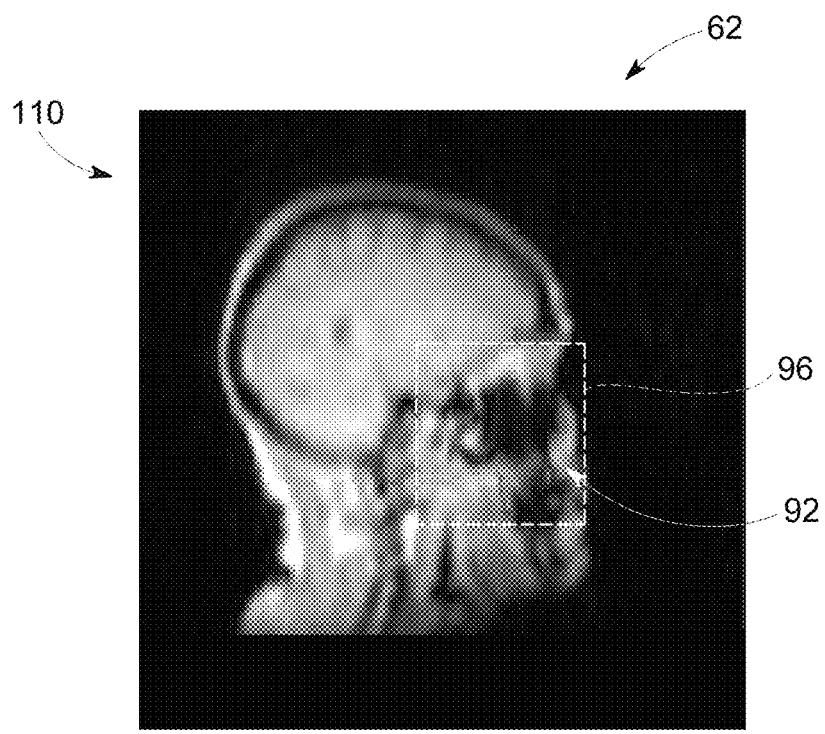
FIG. 10 is another diagram of the second image of the subject of FIG. 9, wherein the second image is acquired via the system of FIG. 1, in accordance with an embodiment of the invention.
Figure 11:
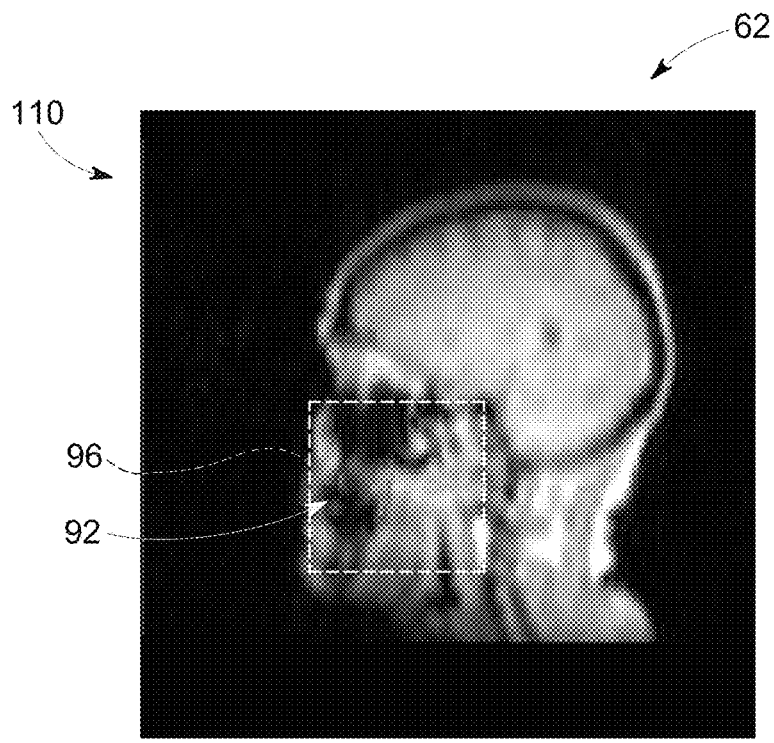
FIG. 11 is yet another diagram of the second image of FIG. 10, wherein the second image has been inversed, in accordance with an embodiment of the invention.

Alternatively, as shown in FIGS. 9 and 10, in embodiments wherein the first image 104 depicts a non-symmetrical anatomy of the subject 62 such that the first image 104 includes the first region 94 but not the second region 96, the second image 110 may be generated 114 (FIG. 3) directly from the MR data 65 and then inversed 116 (FIG. 3) such that the anatomy of the patient 62 depicted in the second image 110 substantially aligns with the anatomy depicted in the first image 104 as shown by FIGS. 9 and 11. For example, FIG. 9 is a first image 104 depicting a left profile view of a subject 62 having a metal dental implant 82 in the left jaw, wherein the left side of the subject's 62 anatomy, i.e., region 94, is not symmetrical to the anatomy on the right side of the image 104. Accordingly, FIG. 10 depicts a second image 110 generated directly from the MR data 65 which depicts a right profile view of the subject 62 wherein there are no metal dental implants in the right jaw. FIG. 11 is the inversion of the second image 110 shown in FIG. 10.

Figure 13:
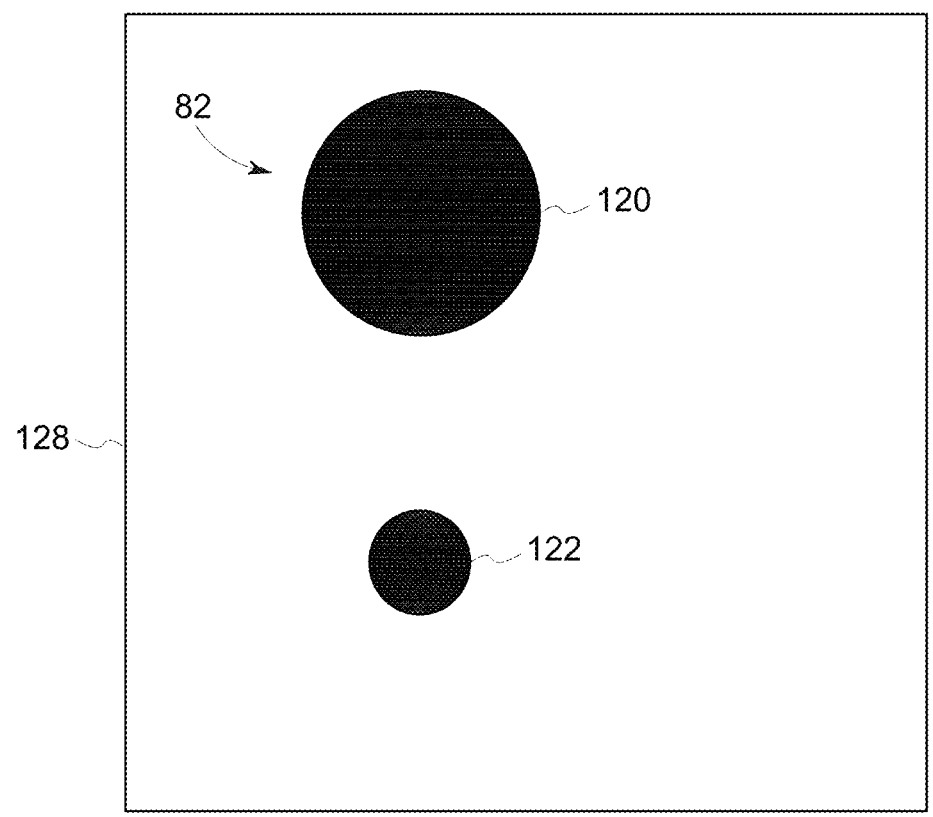
FIG. 13 is a diagram of an asymmetry map generated by the system of FIG. 1, in accordance with an embodiment of the invention.

Once the second image 110 has been generated 108, the intensity values of the first image 104 may then be compared 118 (FIG. 3) to the intensity values of the second image 110 in order to locate regions of contrast 120 and 122 (FIG. 13). As will be appreciated, as artifacts 82 tend to produce low intensity regions within MR data 65, regions containing an artifact 82 will usually result in a high contrast, e.g., a large difference in intensity values, with an anatomically symmetrical region of MR data 65.

In embodiments, the controller 30 may then designate/identify one of the regions of contrast 120 as corresponding to the first portion 88. In embodiments, the region of contrast 120 having the largest continuous area may be identified as the first portion 88, i.e., the region 94 of the subject within which the artifact 82 is disposed.

As will be understood, in embodiments, comparing 118 the intensities of the first image 104 to the second image 110 may include registering 124 the second image 110 to the first image 104 or vice versa. Registering 124 may be accomplished via a 3D rigid registration algorithm, e.g., in-phase LAVA-FLEX in accordance with SIGNA PET/MR.

Embodiments of the invention may also perform additional imaging processing steps to the first image 104, second image 110, and/or a combined/overlaid/registered version thereof. For example, embodiments of the invention may employ one or more thresholds such that only regions of contrast that exceed the threshold may be considered by the controller 30 as corresponding to an artifact 82. Such thresholding may be performed in combination with histogram-based normalization. As will be appreciated, the use of a threshold decreases the chances that the controller 30 will identify a false positive region of contrast, e.g., a region of contrast resulting from differing intensities not derived/caused by an artifact 82, such as a region of contrast resulting from mis-registration between the first 104 and second 110 images. Further, in embodiments, one or more of the images 104, 110 and/or a combined/registered version thereof, may be down-sampled, i.e., resampled at a lower resolution than the original MR acquisition, in order to speed up the comparison of intensity values.

Moving to FIG. 13, the controller 30 may then generate 126 (FIG. 3) an asymmetry map 128 that indicates the location of the regions of contrasts 120, 122. In embodiments, the asymmetry map 128 may be based at least in part on the first 104 and second 110 images, and/or a combined/overlaid/registered version thereof. The asymmetry map 128 may also only depict regions of contrast 120, 122 that exceed an applied threshold. In embodiments, the asymmetry map 128 may be upsampled, in the region corresponding to a region of contrast 120 identified as being an artifact 82, back to the resolution of the originally acquired MR data 65.

As stated above, the controller 30 will populate 86 the first portion 88 with substitute data 90 based on data from the second portion 92. As will be understood, the substitute data 90 may be a copy and/or modified version, i.e., derived from, of the MR data 65 within the second portion 92. In embodiments, the substitute data 90 may be voxels of raw k-space and/or image space, and/or pixels from the second image 110.

Figure 8:
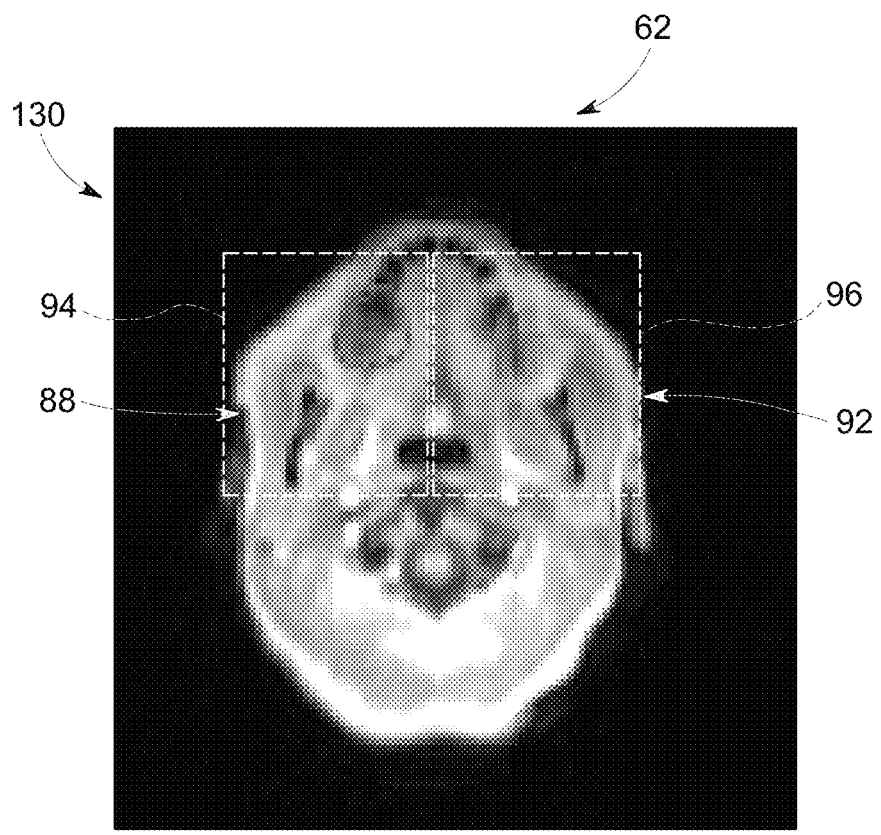
FIG. 8 is a diagram of a corrected image of the subject of FIG. 6 generated by the system of FIG. 1, in accordance with an embodiment of the invention.
Figure 12:
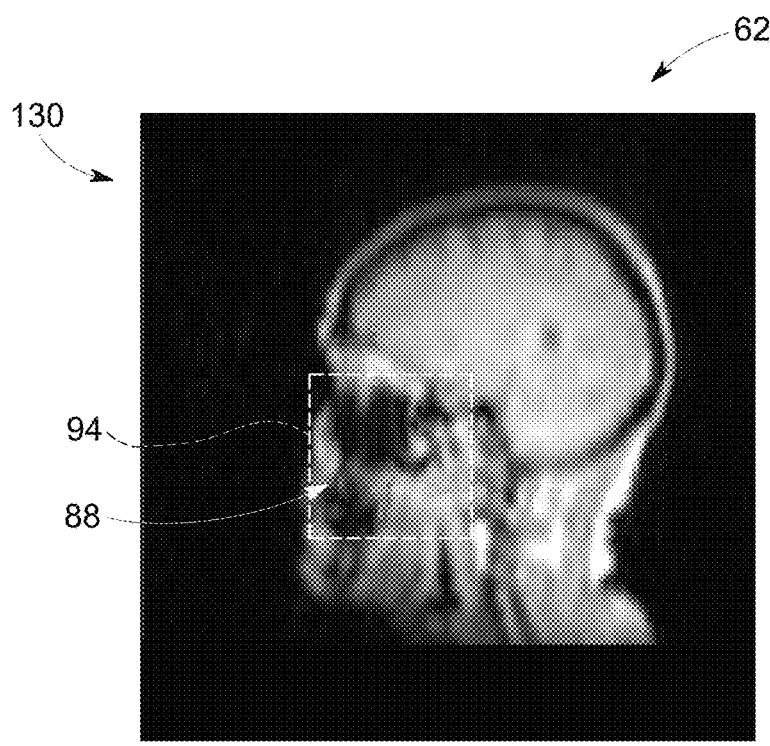
FIG. 12 is a diagram of the corrected image of the subject of FIG. 9 generated by the system of FIG. 1, in accordance with an embodiment of the invention.

Accordingly, as shown in FIGS. 6-8 the substitute data 90 derived from the second portion 92 of the second image 110 (which is shown in FIG. 7 as the inverse of the first image 104 in FIG. 6) is used to populate/replace and/or otherwise augment the MR data 65 within the first portion 88 such that the effects of the artifact 82 are mitigated in a corrected image 130 as shown in FIG. 8. A similar scenario is shown in FIGS. 9-12 in which the controller 30 populates the first portion 88 with substitute data 90 derived from the second portion 92 of the inversed version of the second image 110 (FIG. 11) to populate/replace and/or otherwise augment the MR data 65 within the first portion 88 such that the effects of the artifact 82 are mitigated as shown in the corrected image 130 as shown in FIG. 12.

Once the MR data 65 in the first portion 88 has been populated with the substitute data 90, the controller 30 may then proceed to generate 100 an attenuation model, which in turn, provides for a more complete/accurate model of the anatomy of the subject 62 had the original MR data within the first portion 88, which was affected by the artifact 82, been retained. As will be appreciated, while the first 88 and second 92 portions, first 94 and second 96 regions, and first 104 and second 110 images are shown herein as being 2D, it will be understood that, in embodiment, these may be 3D.

Finally, it is also to be understood that the imaging system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein, which may be accomplished in real-time. For example, as previously mentioned, the system may include at least one processor and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium," as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for correcting an artifact within MR data is provided. The system includes a magnet assembly and a controller in electronic communication with the magnet assembly. The controller is operative to: acquire the MR data from a subject via the magnet assembly, the MR data having a first portion and a second portion, the first portion including the artifact; and to populate the first portion of the MR data with substitute data corresponding to the second portion. The first portion corresponds to a first region of the subject, and the second portion corresponds to a second region of the subject that is anatomically symmetrical to the first region. In certain embodiments, the controller is further operative to receive, via a user input device in electronic communication with the controller, an indicator that identifies at least one of the first portion and the second portion. In certain embodiments, the controller is further operative to identify the first portion. In certain embodiments, the controller is further operative to: generate a first image from the MR data; generate a second image; and compare intensity values of the first image to intensity values of the second image to identify a region of contrast. In such embodiments, the identified first portion corresponds to the region of contrast. In certain embodiments, the first image includes both the first region and the second region, and the controller generates the second image based at least in part on the first image. In certain embodiments, the second image is the inverse of the first image. In certain embodiments, the first image includes the first region, and the controller generates the second image from the MR data such that the second image includes the second region. In certain embodiments, the controller is further operative to generate an asymmetry map based at least in part on comparing the intensity values of the first image to the intensity values of the second image. In such embodiments, the asymmetry map indicates a location of the region of contrast. In certain embodiments, the controller is further operative to generate an attenuation model based at least in part on the first portion when populated with the substitute data.

Other embodiments provide for a method for correcting an artifact within MR data. The method includes: acquiring the MR data from a subject via a magnet assembly in electronic communication with a controller, the MR data having a first portion and a second portion, the first portion including the artifact; and populating, via the controller, the first portion of the MR data with substitute data corresponding to the second portion. The first portion corresponds to a first region of the subject, and the second portion corresponds to a second region of the subject that is anatomically symmetrical to the first region. In certain embodiments, the method further includes identifying, via a user input device in electronic communication with the controller, an indicator that identifies at least one of the first portion and the second portion. In certain embodiments, the method further includes identifying the first portion via the controller. In certain embodiments, identifying the first portion via the controller includes: generating a first image from the MR data; generating a second image; and comparing intensity values of the first image to intensity values of the second image to identify a region of contrast. In such embodiments, the identified first portion corresponds to the region of contrast. In certain embodiments, the first image includes both the first region and the second region, and the controller generates the second image based at least in part on the first image. In certain embodiments, generating a second image includes inversing the first image. In certain embodiments, the first image includes the first region, and the controller generates the second image from the MR data such that the second image includes the second region. In certain embodiments, the method further includes generating, via the controller, an asymmetry map based at least in part on comparing the intensity values of the first image to the intensity values of the second image. In such embodiments, the asymmetry map indicates a location of the region of contrast. In certain embodiments, the method further includes generating an attenuation model based at least in part on the first portion when populated with the substitute data.

Yet still other embodiments provide for a non-transitory computer readable medium storing instructions. The stored instructions are configured to adapt a controller to: acquire MR data from a subject via a magnet assembly, the MR data having a first portion and a second portion, the first portion including an artifact; and to populate the first portion of the MR data with substitute data corresponding to the second portion. The first portion corresponds to a first region of the subject, and the second portion corresponds to a second region of the subject that is anatomically symmetrical to the first region. In certain embodiments, the stored instructions are further configured to adapt the controller to generate an attenuation model based at least in part on the first portion when populated with the substitute data.

Accordingly, as will be appreciated, by exploiting the left/right symmetry of an object, e.g., the human body, some embodiments of the present invention provide for a post-processing approach for correcting one or more artifacts in MR data. Accordingly, some embodiments of the present invention provide for faster, and/or more accurate, attenuation correction in combined PET-MRI than traditional systems and methods.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for correcting an artifact within magnetic resonance (MR) data comprising:
   a radio frequency (RF) coil;
   a controller in electronic communication with the RF coil and operative to:
      acquire the MR data from a subject via the RF coil, the MR data having a first portion and a second portion, the first portion including the artifact;
      populate the first portion of the MR data with substitute data corresponding to the second portion; and
      wherein the first portion corresponds to a first region of the subject, and the second portion corresponds to a second region of the subject that is anatomically symmetrical to the first region.

2. The system of claim 1, wherein the controller is further operative to:
   receive, via a user input device in electronic communication with the controller, an indicator that identifies at least one of the first portion and the second portion.

3. The system of claim 1, wherein the controller is further operative to:
   identify the first portion.

4. The system of claim 3, wherein the controller is further operative to:
   generate a first image from the MR data;
   generate a second image;
   compare intensity values of the first image to intensity values of the second image to identify a region of contrast; and
   wherein the identified first portion corresponds to the region of contrast.

5. The system of claim 4, wherein
   the first image includes both the first region and the second region, and
   the controller generates the second image based at least in part on the first image.

6. The system of claim 5, wherein the second image is the inverse of the first image.

7. The system of claim 4, wherein
   the first image includes the first region; and
   the controller generates the second image from the MR data such that the second image includes the second region.

8. The system of claim 4, wherein the controller is further operative to:
   generate an asymmetry map based at least in part on comparing the intensity values of the first image to the intensity values of the second image, the asymmetry map indicating a location of the region of contrast.

9. The system of claim 1, wherein the controller is further operative to:
   generate an attenuation model based at least in part on the first portion when populated with the substitute data.

10. A method for correcting an artifact within magnetic resonance (MR) data comprising:
    acquiring the MR data from a subject via a radio frequency (RF) coil in electronic communication with a controller, the MR data having a first portion and a second portion, the first portion including the artifact;
    populating, via the controller, the first portion of the MR data with substitute data corresponding to the second portion; and
    wherein the first portion corresponds to a first region of the subject, and the second portion corresponds to a second region of the subject that is anatomically symmetrical to the first region.

11. The method of claim 10 further comprising:
    identifying, via a user input device in electronic communication with the controller, an indicator that identifies at least one of the first portion and the second portion.

12. The method of claim 10 further comprising:
    identifying the first portion via the controller.

13. The method of claim 12, wherein identifying the first portion via the controller comprises:
    generating a first image from the MR data;
    generating a second image;

comparing intensity values of the first image to intensity values of the second image to identify a region of contrast; and wherein the identified first portion corresponds to the region of contrast.

14. The method of claim 13, wherein the first image includes both the first region and the second region, and the controller generates the second image based at least in part on the first image.

15. The method of claim 14, wherein generating a second image comprises:

inversing the first image.

16. The method of claim 13, wherein

The first image includes the first region; and the controller generates the second image from the MR data such that the second image includes the second region.

17. The method of claim 13 further comprising:

generating, via the controller, an asymmetry map based at least in part on comparing the intensity values of the first image to the intensity values of the second image, the asymmetry map indicating a location of the region of contrast.

18. The method of claim 10 further comprising:

generating an attenuation model based at least in part on the first portion when populated with the substitute data.

19. A non-transitory computer readable medium storing instructions configured to adapt a controller to:

acquire magnetic resonance (MR) data from a subject via a radio frequency (RF) coil, the MR data having a first portion and a second portion, the first portion including an artifact;

populate the first portion of the MR data with substitute data corresponding to the second portion; and wherein the first portion corresponds to a first region of the subject, and the second portion corresponds to a second region of the subject that is anatomically symmetrical to the first region.

20. The non-transitory computer readable medium of claim 19, wherein the stored instructions are further configured to adapt the controller to:

generate an attenuation model based at least in part on the first portion when populated with the substitute data.

* * * * *